(12) United States Patent
Pefferman (10) Patent No.: US 10,512,320 B1
(45) Date of Patent: Dec. 24, 2019

(54) COSMETIC FACE MASK AND KIT

(71) Applicant: Julie Pefferman, San Diego, CA (US)

(72) Inventor: Julie Pefferman, San Diego, CA (US)

( * ) Notice: Subject to any disclaimer, the term of this patent is extended or adjusted under 35 U.S.C. 154(b) by 415 days.

(21) Appl. No.: 15/078,803

(22) Filed: Mar. 23, 2016

(51) Int. Cl.
*A45D 44/00* (2006.01)
*A61M 35/00* (2006.01)
*A61M 19/00* (2006.01)

(52) U.S. Cl.
CPC .......... *A45D 44/002* (2013.01); *A61M 19/00* (2013.01); *A61M 35/00* (2013.01); *A61M 2202/048* (2013.01); *A61M 2210/0606* (2013.01)

(58) Field of Classification Search
CPC . A45D 44/002; A61F 2007/003; A61F 35/00; A61F 9/04; A61F 2007/0003; A61F 35/002; A61M 35/00; A61M 35/006; A61M 35/10; A61M 2210/0606
USPC ........................................................ 604/303
See application file for complete search history.

(56) References Cited

U.S. PATENT DOCUMENTS

| | | | | | |
|---|---|---|---|---|---|
| 4,527,565 | A | * | 7/1985 | Ellis ........................... | A61F 7/10 607/109 |
| 5,623,733 | A | * | 4/1997 | Kurimoto ............ | A45D 44/002 132/319 |
| 6,241,711 | B1 | * | 6/2001 | Weissberg ................. | A61F 7/10 604/291 |
| 6,503,232 | B1 | * | 1/2003 | Kawai .................... | A61F 13/126 602/48 |
| 9,011,394 | B2 | * | 4/2015 | Gueret ................. | A61K 8/0212 132/320 |
| 2002/0192269 | A1 | * | 12/2002 | Beyer .................. | A61K 8/0208 424/443 |
| 2003/0015205 | A1 | * | 1/2003 | Lai ........................ | A45D 44/002 128/857 |
| 2004/0013828 | A1 | * | 1/2004 | Tewes-Schwarzer ........................ A45D 44/002 428/34.1 |
| 2005/0192653 | A1 | * | 9/2005 | Tsunakawa ............. | A61F 7/034 607/109 |
| 2006/0048278 | A1 | * | 3/2006 | Pitsolis ................ | A45D 44/002 2/206 |
| 2008/0051860 | A1 | * | 2/2008 | Wyk .................... | A45D 44/002 607/109 |
| 2009/0041815 | A1 | * | 2/2009 | Legendre ............. | A61K 8/0208 424/401 |
| 2009/0241242 | A1 | * | 10/2009 | Beatty .................. | A45D 44/002 2/206 |
| 2010/0228204 | A1 | * | 9/2010 | Beatty .................. | A45D 44/002 604/303 |

(Continued)

OTHER PUBLICATIONS

"Plastics—Thermal Conductivity Coefficients," www.EngineeringToolBox.com, printed May 15, 2018.*

(Continued)

*Primary Examiner* — Susan S Su
(74) *Attorney, Agent, or Firm* — Simana Rao, Esq.

(57) ABSTRACT

This invention relates to reusable, multi-layered articles having the ability to maintain a desired temperature and be used for cosmetic and/or medical applications. In particular, the invention is directed to cosmetic facial masks and kits used to treat the skin of a user by applying heat or cold along with an optional therapeutic composition, and maintain the desired temperature during the duration of treatment. The multi-layered article is designed to be reusable, washable and sterilizable.

19 Claims, 3 Drawing Sheets

(56) References Cited

U.S. PATENT DOCUMENTS

| | | | |
|---|---|---|---|
| 2013/0096515 A1* | 4/2013 | Montrose | A61K 8/31 604/290 |
| 2014/0005616 A1* | 1/2014 | Moreland | A61L 15/44 604/292 |
| 2014/0318565 A1* | 10/2014 | Ito | A45D 44/002 132/200 |
| 2015/0173487 A1* | 6/2015 | Wardaszka | A61F 9/04 604/303 |
| 2016/0089308 A1* | 3/2016 | Mohammadi | A61K 8/0212 604/20 |
| 2016/0242959 A1* | 8/2016 | Waugh | A61F 7/12 |
| 2016/0346529 A1* | 12/2016 | Cazares Delgadillo | A61N 1/0412 |
| 2017/0231813 A1* | 8/2017 | Huang | A61F 7/034 607/109 |
| 2017/0246445 A1* | 8/2017 | Planard-Luong | A61N 1/044 |

OTHER PUBLICATIONS

"Thermal Conductivity of Common Materials and Gases," www.EngineeringToolBox.com, printed Jan. 24, 2019. (Year: 2019).*

* cited by examiner

COSMETIC FACE MASK AND KIT

TECHNICAL FIELD OF THE INVENTION

This invention relates to reusable, multi-layered articles having the ability to maintain a desired temperature and be used for cosmetic and/or medical applications. In particular, the invention is directed to cosmetic facial masks and kits used to treat the skin of a user by applying heat or cold along with an optional therapeutic composition, and maintain the desired temperature during the duration of treatment. The multi-layered article is designed to be washable and capable of repeated sterilization, and is thus reusable.

BACKGROUND OF THE INVENTION

Cosmetic treatment articles including masks designed for providing treatment to the skin are known in the art. In some instances, a facial mask is the application of a liquid or gel covering directly onto the face. This allows the mixing and application of a variety of topical treatments to the skin being treated. In other instances, a facial mask may be created by saturating a cloth-like material with a particular topical treatment composition. This homogeneous treatment can then be applied to the face such that the topical treatment(s) on the cloth-like material will contact the face.

Sometimes, facial masks are applied to the user's face, and then covered by a warm towel to heat and activate the mask solutions, and to improve absorption of the solution into the skin. These warm towels may serve to activate the solutions; however, the towels tend to cool quickly so that the mask returns to room temperature long before the facial treatment is over. Alternatively, it is often advantageous to provide a cooling facial mask. Currently, these cooling facial masks are applied with a cool towel, which when applied to the person's skin, quickly warm up to ambient temperature due to the warmth of the user's skin and the surrounding air temperature. The use of ice, while appropriate in a trauma situation, is impractically cold for a relaxing facial treatment.

Various methods have been used in the past to apply heating and/or cooling treatment to a facial mask. U.S. Pat. No. 2,705,952, which is incorporated by reference in this application, provides a mask with a water chamber to house either cold or hot water. Such a method is messy and does not provide the user with adequate means of keeping the desired temperature for the entire duration of treatment. U.S. Pat. No. 8,372,130 provides a facial mask which can be heated by employing a layer containing a swellable hydrophilic polymer and a magnesium-iron active mineral compound which, when mixed together in the presence of water and salt produces an exothermic reaction for about an hour. This kind of heating mask, however, requires a chemical reaction to take place and therefore can only be used once by the user. Users are forced to purchase product after product to treat their skin, which can be costly and contribute to environmental waste.

Reusable facial masks which can be heated for a sustained amount of time are limited to electric or battery powered facial masks and also gel pack facial masks, each of which are associated with disadvantages. Electrical and battery powered masks require a voltage source to heat the mask, such as that which is disclosed in CN2286043, which is incorporated by reference in this application. This method produces a bulky, complicated assembly which is expensive for the user to employ, as well as potentially hazardous for the user to apply in conjunction with water or liquid based compositions due to the power source.

U.S. Pat. No. 8,636,786 which is also incorporated herein by reference, uses a thermally adjustable gel pack which can be first heated or cooled and next inserted into a fabric mask or eye patch to provide the desired heating or cooling. One or more gel packs are used which are secured to a support structure and is held against the face. However, the use of gel packs in conjunction with facial treatment is associated with disadvantages. First, insertion of the gel pack creates a heavy, bulky mask which is difficult to bend and conform to the face and therefore does not facilitate even and uniform heating throughout the face. The consistency and rheology of gels are also not designed to conform to the contours of the face. Second, the plastic (generally polyethylene) outer cover that is typical of gel packs is not permeable to air and therefore does not allow the skin to breathe. Furthermore, typical facial compress designs incorporating gel packs require multiple parts which can be lost by the user, or damaged in some way which leaves the user with an incomplete facial treatment regimen. The gel pack is also generally unaesthetically pleasing to the user.

There is therefore a need for a reusable, washable facial mask which can be easily heated or cooled and maintain a desired temperature for the entire duration of facial treatment, such as up to one hour or more. It is further an object of this invention to create a facial mask which is light weight, has a simple design and is aesthetically pleasing to the user.

SUMMARY

In one general aspect there is provided a kit for treating the skin which includes a facial mask having a skin contacting layer and an insulating layer, the skin contacting layer having a skin contacting surface and an inside surface and the insulating material having an outside surface and an inside surface, the inside surface of the skin contacting layer being in substantial contact with the inside surface of the insulating material, wherein the two layers are secured together along the perimeter of the layers to form a multiple layered article, a container which houses the mask, optionally, a treatment composition to apply to the mask, and, written or graphic instructions for use of the mask including the following steps: moistening the layered article with water or the optional treatment composition, heating or cooling the layered article, placing the layered article on the skin for an amount of time, removing the layered article from the skin, and washing the layered article to use it again.

Embodiments of the kit may include one of the following features. The instructions may be provided in the form of an html address which provides the steps for use of the mask. The instructions may be provided in the form of an html address which includes a video demonstration of use of the mask. The kit may further include one or more photographs or drawings depicting one or more steps of use of the mask. The insulating material may be formed of foam, neoprene, or a fiberglass material. The step of heating the layered article may include microwaving the article. The step of cooling the layered article includes placing the article in the freezer or the refrigerator. The step of moistening the layered article may include placing the article in the container along with an amount of water. The step of heating the layered article may include subjecting the container having the layered article and water within it to microwaves.

The step of cooling the layered article may include placing the container having the layered article and water within it into a refrigerator or freezer. The step of washing the layered article may include machine washing. The insulating layer may have a k value of about 0.01 to about 1 W/m K. The facial mask may further include a mesh layer with a total open area of between 30% and 95%. The facial mask may be a single article having a substantially circular shape with one or more openings to accommodate the eyes, mouth or nose of a user.

The facial mask may include one or more slits starting at the perimeter of the mask and ending at a point closer to the center of the mask in order to accommodate a number of face sizes. The instructions may further include a step of keeping the layered article on the skin for about thirty minutes to about one hour. The facial mask may further include a foam layer and a silicon fiberglass layer. The insulating layer may include a neoprene layer. The facial mask may further comprises a gel layer.

In another general aspect there is provided a method of treating the face, including providing a reusable, washable facial mask having a skin contacting layer and an insulating layer, the skin contacting layer having a skin contacting surface and an inside surface and the insulating material having an outside surface and an inside surface, the inside surface of the skin contacting layer being in substantial contact with the inside surface of the insulating material, wherein the two layers are secured together along the perimeter of the layers to form a multiple layered article, a step of moistening the layered article with water or an optional treatment composition, a step of heating or cooling the layered article, a step of placing the layered article on the skin for an amount of time, and, a step of removing the layered article from the skin.

DETAILED DESCRIPTION

Figure 1:
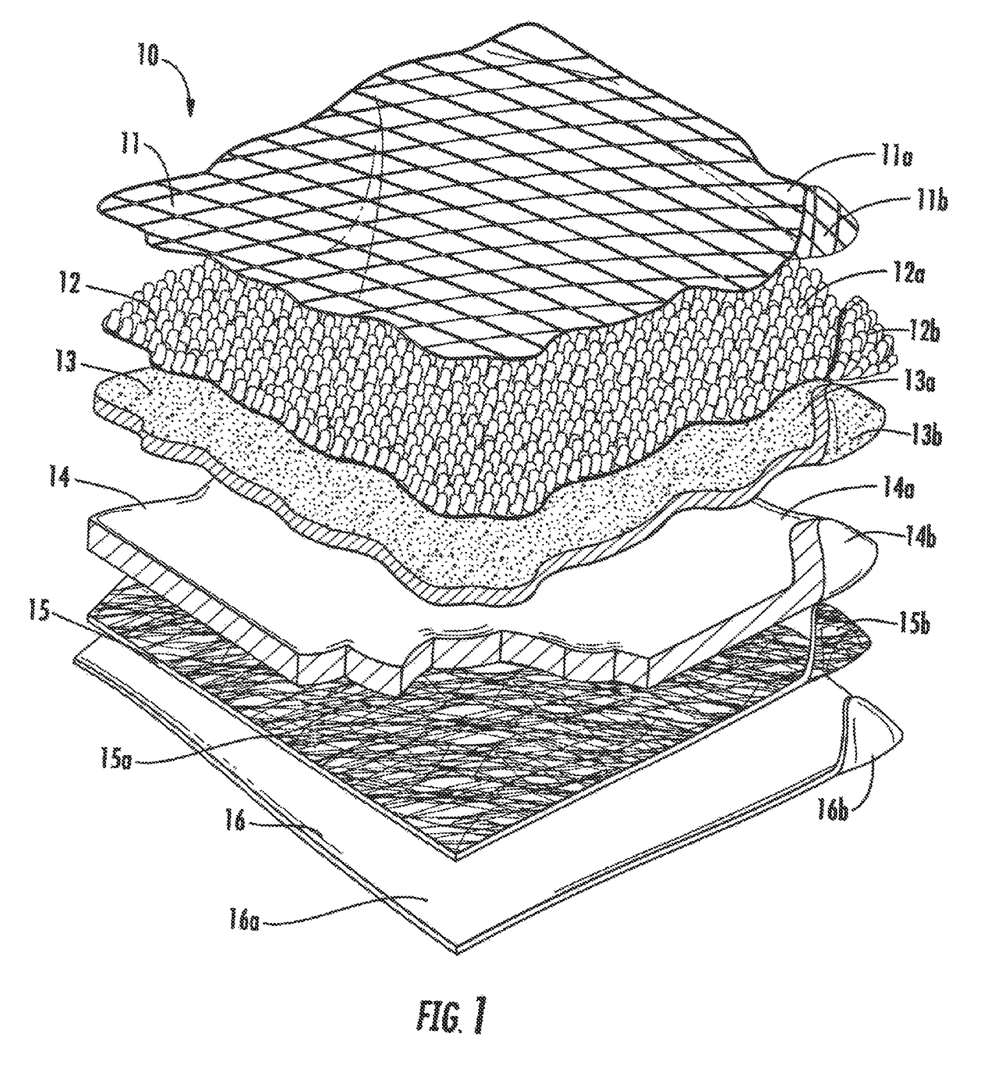
FIG. 1 is an exploded view of a section of the facial mask of the present invention, having six layers, four of which are optional.
Figure 2:
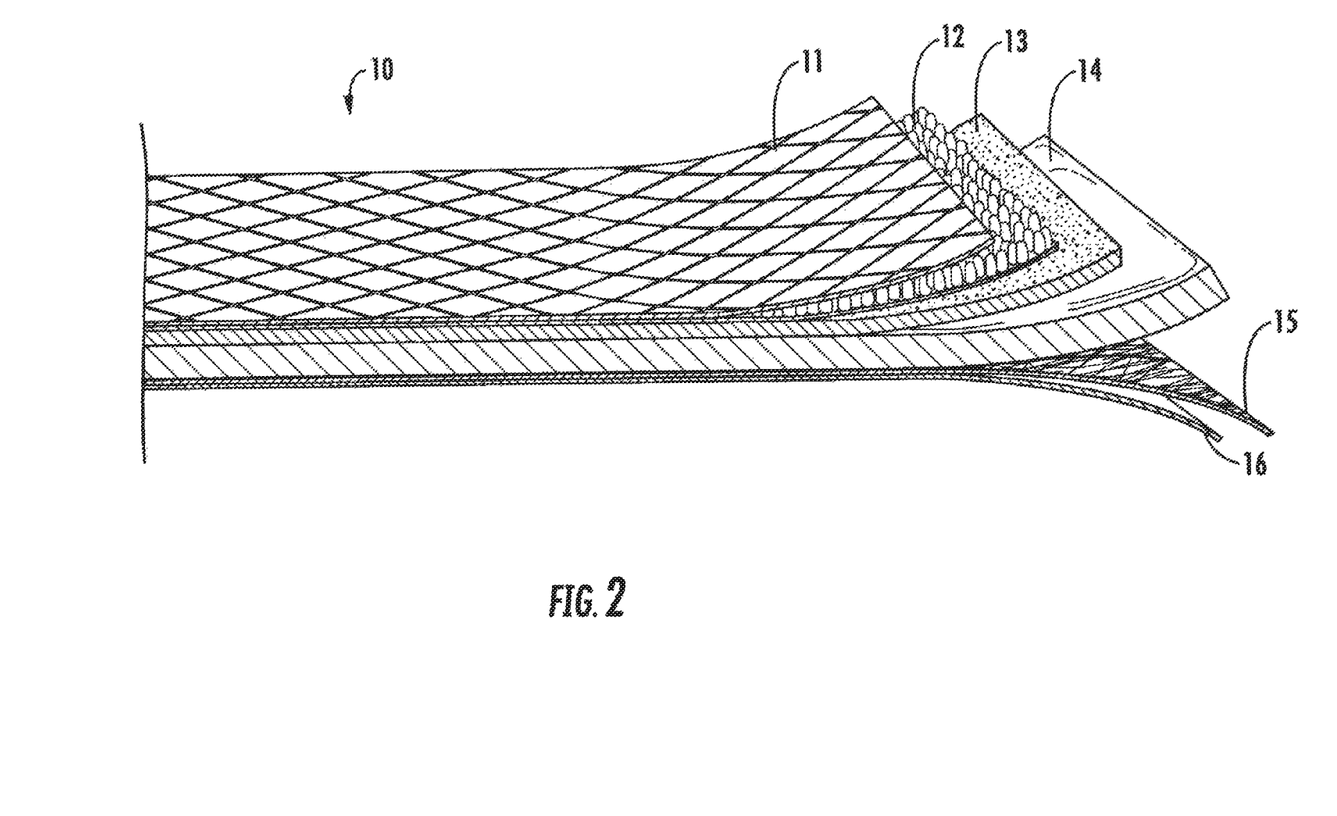
FIG. 2 is a side view of the layers of the facial mask of the present invention.
Figure 3:
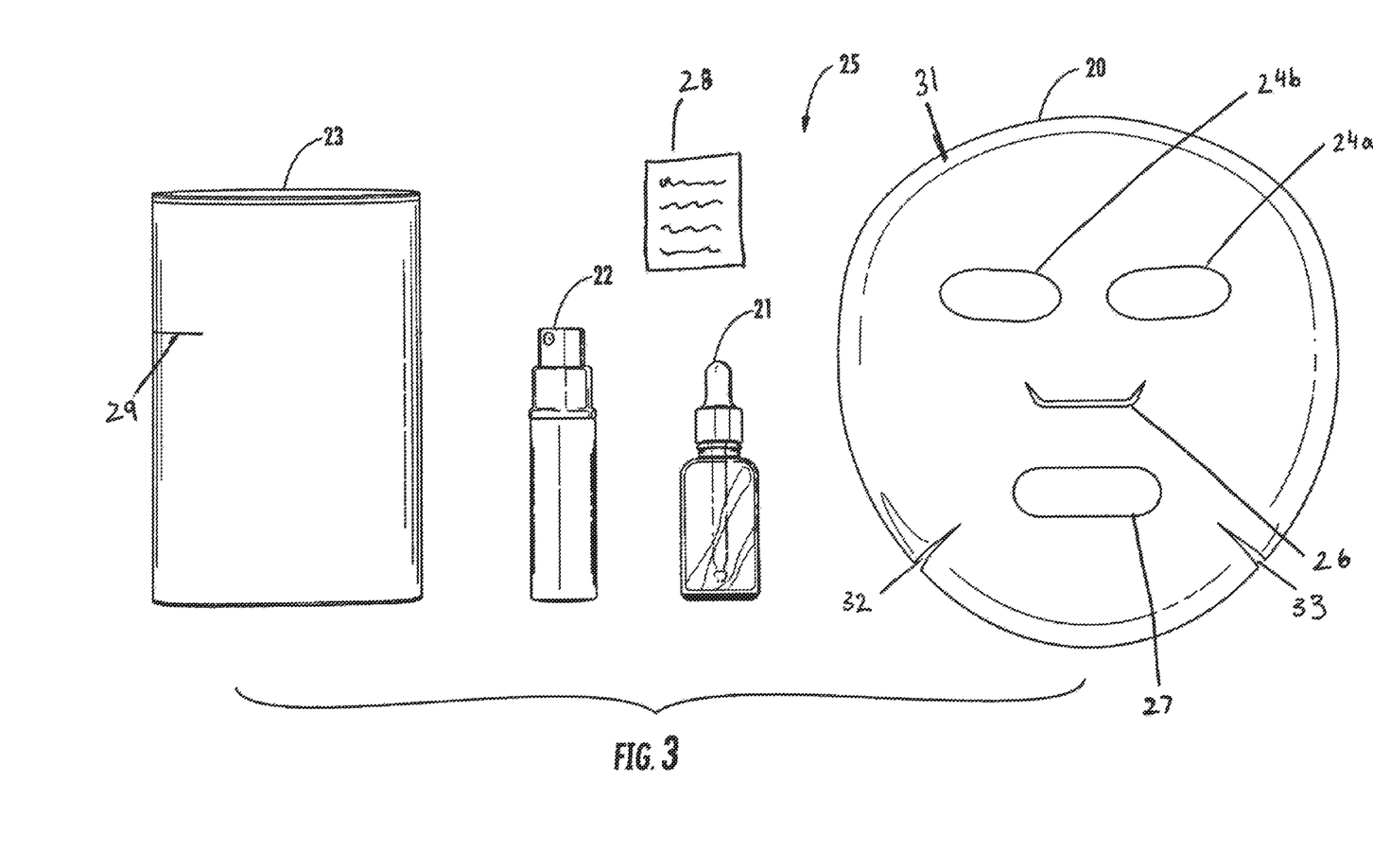
FIG. 3 illustrates a facial mask kit of the present invention. This kit is an example of the items which may be included and is not intended to be limited to the items shown.

Referring to FIGS. 1-3 is a facial mask article which may be used to apply heat or cold treatment and an optional therapeutic composition to the face and surrounding areas of a user, such as the neck and decollette of the user. The facial mask preferably includes two or more layers, with one layer being a soft cloth face contacting layer and the other layer being the outside insulating layer which serves to aid in maintaining the desired temperature of the mask. Maintaining a high temperature of the mask including the soft cloth face contacting layer provides many benefits including to open up pores of the skin to allow maximum and efficient penetration of therapeutic product or steam, remove toxins, moisturize the skin, and provide a relaxing feeling to the user.

Preferably, when used in heated form, the mask is designed to maintain a temperature of between 85° and 130° F. for up 10 minutes, more preferably for up to 30 minutes and most preferably for up to one hour. When the mask is used in cold form, the mask is designed to maintain a temperature of between about 32° and 84° F. for up to 10 minutes, more preferably for up to 30 minutes and most preferably for up to one hour. The cooling facial mask is preferable to provide the user with a cooling sensation to relieve certain skin ailments and conditions, such as sun burn and redness of the skin, puffy eyes, and acne.

Furthermore, depending on the temperature preference of the user, the temperature variation of the mask is minimized in comparison with prior art single layer facial towels. For example, the temperature fluctuation from time 1 to time 2 is preferably no more than 30° F., more preferably no more than 15° F., and most preferably 10° F. or less, with time 1 being the time that the mask is initially cooled or heated, and time 2 being anywhere between 5 minutes and 60 minutes later.

In use, the facial mask may be provided alone or in a kit form such as kit 25 shown in FIG. 3. The kit may include a mask 20 which has eye cut-out portions 24a and 24b, nose cut-out portion 26, and mouth cut-out portion 27, a container 23, spray bottle 23 containing a therapeutic composition, dropper bottle 21 containing a therapeutic composition, and instructions for use 28. Preferably, the kit is provided to enable a user to conveniently have an "at home" facial without having to visit a spa. The kit may optionally be sold with various therapeutic treatments such as is shown in spray bottle 22 and dropper bottle 21, which may target certain areas or conditions the user wishes to treat, such as dry skin or wrinkles. Particular therapeutic compositions will be discussed later on in this detailed description.

The kit 25 preferably includes instructions 28 in either written form as shown in FIG. 3, or in electronic form such as on a website, online video or digital memory drive. The instructions may also be in written directly on the packaging container 23. The instructions provide the steps for using the beauty mask 20. The first step may be the heating or cooling step. The mask may be dampened with water in a vessel, which is either provided within kit 25, or supplied by the user. In one embodiment, the container 23 is a container which is designed to hold water which is to be heated or cooled and may hold the mask. The container may also be microwave safe, stove top safe and/or freezer safe. In one embodiment, a container includes a fill line 29 showing how much water to fill the container with. The container may then be placed in the microwave for a certain amount of time in order to achieve the desired level of heating. Instructions may be provided which are dependent on the user's microwave wattage.

In one embodiment, the container and the mask immersed in water is heated in the microwave at the same time. In another embodiment, the container and water are heated separately in the microwave and at a later time the mask is added to the container after the water is heated. For example, the container may be heated in a 1,000 watt microwave for less than 90 seconds, preferably less than 60 seconds, and more preferably for less than 45 seconds. A higher watt microwave would mean that the heating time would be less than that just taught, and a lower watt microwave would mean that the heating time would be more than that just taught. The water is heated either by microwave or stove top, or the water may be boiled in a kettle and poured into the container.

In one embodiment a thermometer is provided in the kit to enable the user to determine the temperature of her facial mask. The thermometer may be a paper thermometer which is adhesively attached to the inside or the outside of the container, such as that which is sold by PaperThermometer®. In another embodiment, a label or heat sensitive sticker may be attached which includes a color indicator showing the user that the water temperature has reached a certain predetermined temperature and therefore the mask can be applied.

Next in the instructions is preferably a step of waiting for the mask to achieve the desired temperature and completely penetrate the heated water. This time period may be from about 0-30 minutes, depending on the desired temperature of the user.

The mask may also be cooled instead of heated. In this embodiment, the instructions include a step of filling the container to the fill line 29 with water, immersing the mask in the water, and placing the container in the refrigerator or freezer for an amount of time. For example, the container may be placed in the freezer for 15 minutes or more, preferably 30 minutes or more, and more preferably for 1 hour or more.

Next in the instructions is to lay back the user's head in a direction substantially parallel to the floor and place the mask 20 on the face of the user such that the face contacting layer is touching the face of the user and the outer side of the insulating layer faces upwards. As stated above, the facial mask is designed to maintain the desired temperature of the user and may be placed for an extended amount of time in comparison to prior art towels. Furthermore, the temperature fluctuation achieved with this multi-layered mask is minimal, as is explained above. The mask may then be removed by the user according to the time periods specified or at the discretion of the user.

Important in this multi-layered facial mask is the ability of the mask to be washed and re-used. Instructions which come in the kit preferably note this characteristic of the mask. The mask may be hand washed but may also be machine washed and dried as is convenient for the user. This is an important difference between prior art multi-layered facial masks as most are designed to either disintegrate over time on the face or be disposed of after one application. The present invention thus provides the user with an environmentally friendly, cost effective method of having an at-home facial while also being able to come close to professional quality results because of the ability to maintain a hot or cold temperature for a prolonged amount of time, i.e., up to one hour, with minimal temperature fluctuation.

The mask 20 is small and lightweight in comparison to prior art temperature controllable masks, without any separate parts that need to be handled, removed and cleaned separately. Therefore, there is a much less likelihood of missing parts, and the mask does not impose a storage problem to the user.

Each of the layers of the mask 20 will now be discussed in detail.

Microfiber Layer:

Shown in FIGS. 1 and 2 is the microfiber layer 12, which is one example of the face contacting layer. This layer includes a skin contacting side 12*a* and an inner side 12*b*. Microfiber is typically a blend of polyester and polyamide. The microfiber fabric of the present invention may be constructed of a blend of 80/20, 75/25, 70/30, 60/40 or 50/50 ratios of polyester/polyamide (examples of polyamide are nylon, Kevlar, Nomex, trogamide), or a conjugation of polyester, polyamide, and polypropylene (Prolen). Alternatively, the microfiber can be up to 100% polyester.

A particular type of microfiber in an exemplary embodiment is a blend of microscopic polyester and polyamide fiber which is split and then woven into hooks and loops to create tiny scoops that attract particles and absorb liquid. The microfiber cloth may be double-sided with the hooks above-mentioned hooks and loops or may be single sided.

Example microfiber patents include U.S. Pat. No. 7,044,173 titled Microfiber Towel with Cotton Base; U.S. Pat. No. 6,258,455 titled Antimicrobial Ultra-micro fiber Cloth; and U.S. Pat. No. 4,525,411 titled Cleaning Cloth, which are all herein incorporated in their entirety by reference.

The microfiber layer may be woven or non-woven to the extent that the layer remains hand washable or machine washable. A woven microfiber layer is preferred as typically a non-woven microfiber layer is associated with a disposable article which cannot be reused. Therefore, a woven layer is preferred since the multi-layered mask is designed to be washable and reusable.

The microfiber layer of the present invention preferably has a denier of 1 denier or less and a fiber diameter of 10 microns or less. This gives the layer an airy weight, downy feel, and soft, silky texture. Denier is a unit of measurement that is used to determine the fiber thickness of individual threads or filaments used in the creation of textiles and fabrics. Denier is defined as the mass in grams per 9000 meters. Fabrics with a high denier count tend to be thick, sturdy, and durable. Fabrics with a low denier count tend to be sheer, soft, and silky.

The microfiber of the present invention also has superior absorption properties due to its small fiber diameter. This is because the microfiber's small diameter which translates into a much larger surface area than that found in conventional fibers. The small diameter of the fibers also provides a particularly powerful capillary action, which, in addition to pulling in liquid, also pulls in particulates and microbes contained within the liquid. Thus, the combination of the increased surface area and capillary action gives the microfiber cloth the ability to absorb vast amounts of liquid many times its own weight.

Mesh Layer:

Shown in FIGS. 1 and 2 is an optional mesh netting layer 11 having various sizes of openings 30, such as honeycomb, hexagon, diamond, square, circle and oval shaped openings, with a total open area of between 30% and 95%, and/or approximately 2 to 1,000 holes per centimeter squared. Openings 30 may have an area of about 0.1 mm$^2$ to about 100 mm$^2$ and the area may vary within this range from opening to opening.

The mesh netting layer has a skin contacting surface 11*a* and an inside surface 11*b*. The inside surface 11*b* is configured to align with the skin contacting surface 12*a* of the microfiber layer and the two layers are secured to one another preferably along the perimeter of the layers by stitching or adhesive. As the mesh netting contains openings 30, it contacts with the skin of the user and also allows the soft microfiber layer to contact the skin of the user thereby depositing therapeutic agent or water contained therein when placed on the user's face. The mesh layer serves to distribute heat and create a uniform temperature of the mask across the entire surface of the skin contacting surface 12*a* of the microfiber layer. This ensures that the number of hot spots or cold spots are minimized along the surface of the mask and the user experiences a comfortable facial at his or her desired temperature level. The mesh layer may cover the entire surface of the microfiber layer, or in another embodiment may only cover a portion of the microfiber layer.

The mesh is preferably made of a hydrophobic material, or in other words a non-absorbent material. Advantageously, a synthetic material such as polyamide is selected in preference to cotton, although cotton can certainly be used as well. It is also preferable to use a mesh made of material that can be sterilized at a high temperature or during washing. The netting layer 11 is preferably made of synthetic fibers, such as nylon, polyester, or polypropylene and mixtures thereof. Alternatively, the mesh netting may be made of a metal material, such as stainless steel, aluminum, or a composite thereof.

The mesh netting may comprise a woven or nonwoven fabric having a thickness between 0.01 and 2 mm. Preferably a mesh of woven fabric is used, as woven meshes tend to mold better to the various shapes of the body than do nonwoven ones.

Insulating Layer:

Shown in FIGS. 1 and 2 are various types of insulating layers to be used in conjunction with microfiber layer 12 to provide superior temperature control characteristics and minimize fluctuation of temperature from the initial cooled or heated state. At least one out of the four insulating layer is preferably used in conjunction with the microfiber layer 12. In another embodiment, two or more insulating layers may be used in conjunction with the microfiber layer to provide additional insulation or other characteristics as will be described below.

Layer 13 is constructed of neoprene, layer 14 is a gel layer, layer 15 is constructed of foam and layer 16 is a vinyl or fiberglass layer. Each layer will be discussed in detail below.

The neoprene or polychloroprene layer 13 is a family of synthetic rubbers that are produced by polymerization of chloroprene. Neoprene exhibits good chemical stability and maintains flexibility over a wide temperature range. Advantageously, neoprene exhibits excellent thermal insulation properties, having a k value of 0.15-0.50 W/m K. K is a thermal conductivity unit defined as the quantity of heat transmitted through a unit thickness of a material—in a direction normal to a surface of unit area—due to a unit temperature gradient under steady state conditions. The lower the k value of a material, the greater insulation is provided by the material.

The neoprene layer 13 includes a top surface 13a and a bottom surface 13b. In one embodiment, the top surface 13a is configured to align with the inside surface 12b of the microfiber layer and the two layers are secured to one another preferably along the perimeter of the layers by stitching or adhesive. The neoprene layer may also be adhesively applied to another layer across its entire surface area, either 13a and/or 13b. The neoprene layer 13 preferably has a thickness of about 0.01 mm to about 100 mm.

The neoprene layer 13 may be secured to the microfiber layer, or any other layer of the mask, such as layer 11, layer 14, layer 15, layer 16, or an additional layer.

Shown in FIGS. 1 and 2 is gel layer 14 constructed a plastic outer cover having a top surface 14a and a bottom surface 14b with a thermally adjustable gel 14c sealed within. Gel packs may be made of primarily water, hydroxyethyl cellulose, sodium polyacrylate, silica gel or vinyl-coated silica gel. In one embodiment, the top surface 14a is configured to align with the inside surface 12b of the microfiber layer and the two layers are secured to one another preferably along the perimeter of the layers by stitching or adhesive. The gel layer may also be adhesively applied to another layer across its entire surface area or portions of its surface area, either 14a and/or 14b. The gel is sealed within the top surface and bottom surface of the gel pack so that no leakage occurs. The gel layer 14 preferably has a thickness of about 5 mm to about 50 mm. Advantageously, the optional gel packs used with the present invention exhibits excellent thermal insulation properties.

The gel layer 14 may be secured to the microfiber layer, or any other layer of the mask, such as layer 11, layer 13, layer 15, layer 16, or an additional layer.

Shown in FIGS. 1 and 2 is foam layer 15 having top surface 15a and bottom surface 15b. The foam layer may be constructed of a variety of materials, such as polyester, polyether, polyethylene and polyurethane, for example, and may be an open or closed cell foam. A closed cell structure may provide a higher insulation properties than an open cell structure, while an open cell structure provides a more water and vapor permeable layer. Preferably, the foam layer used in conjunction with the present invention has a k value of about 0.01 to 0.05 W/m K.

In one embodiment, the top surface 15a is configured to align with the inside surface 12b of the microfiber layer and the two layers are secured to one another preferably along the perimeter of the layers by stitching or adhesive to form a seam. The foam layer may also be adhesively applied to another layer across its entire surface area or portions of its surface area, either 15a and/or 15b. The foam layer 15 preferably has a thickness of about 0.1 mm to about 50 mm.

The foam layer 15 may be secured to the microfiber layer, or any other layer of the mask, such as layer 11, layer 12, layer 13, layer 16, or an additional layer.

Shown in FIGS. 1 and 2 is a vinyl or fiberglass layer 16, such as a silicon coated fiberglass material. In one embodiment, the top surface 16a is configured to align with the inside surface 12b of the microfiber layer and the two layers are secured to one another preferably along the perimeter of the layers by stitching or adhesive to form a seam. The foam layer may also be adhesively applied to another layer across its entire surface area or portions of its surface area, either 16a and/or 16b. The vinyl or fiberglass layer 16 preferably has a thickness of about 0.1 mm to about 50 mm. Preferably, the fiberglass or vinyl layer used in conjunction with the present invention has a k value of about 0.01 to 0.5 W/m K.

The vinyl or coated fiberglass layer 16 may be secured to the microfiber layer, or any other layer of the mask, such as layer 11, layer 12, layer 13, layer 15, or an additional layer.

Preferably, the thermal conductivity of each layer is optimized such that effective insulation properties are delivered to the multi-layered mask. K is a thermal conductivity unit defined as the quantity of heat transmitted through a unit thickness of a material—in a direction normal to a surface of unit area—due to a unit temperature gradient under steady state conditions. Therefore, in addition to or instead of the layers provided above, other layers may be implemented that would not depart from the spirit of the present invention.

For example, a metallized layer is also contemplated in the invention, such as a layer having metallic fibers interwoven or dispersed through the layer, such as Insul-Bright™ needlepunched insulated lining, Wrap-N-Zap™ cotton batting or other type of metallized fabric.

Shape of Mask:

The mask 20 is shown in FIG. 3 which has a substantially circular shape with openings 24a and 24b for the eyes, opening 26 for the nose, and opening 27 for the mouth of the user. Mask 20 is shown as a single article having a seam 31 which is formed by stitching along the perimeter of the layers, or securing the layers together using adhesive as is known in the art. The seam may be about 1 mm wide up to about 10 mm wide to ensure each layer is secure. One or more slits 32 and 33 are provided which aid in the proper placement and fitting of the mask on the user's face.

It may also be provided that this mask is made in two or more parts, one corresponding to the forehead and extending along its lower edge between two curved cuts that follow the contour of the eyebrow arch and along a flap intended to cover the skin of the nose, and the other part corresponding to the region of the face located below the eyes and including two openings respectively corresponding to the mouth and the nose, the upper edge of this part of the mask including two curved cuts intended for following the lower line of the eyes. These two-piece multi-layered masks adjust well to different face shapes.

As discussed earlier, the mask of the present invention has been developed to improve upon prior art reusable masks. One feature which is particularly beneficial is the lightweight quality of the multi-layered mask while still having the ability to efficiently maintain the desired temperature of the mask. For example, the mask of the present invention is preferably less than 2 pounds, more preferably less than 1.5 pounds and most preferably less than 1 pound. This allows the reusable mask to maintain a relaxing and pleasant experience to the user during the facial process.

Method of Manufacture:

The multi-layered mask of the present invention is made by first cutting and sizing each layer making up the mask, such as the mesh layer 11, the microfiber layer 12, neoprene layer 13, gel pack layer 14, foam layer 15 and/or vinyl/fiberglass layer 16. Two or more of these layers are cut into a substantially circular shape, or may alternatively be made into a different shape, such as a square, oval or rectangle. The cut layers may then be secured together such that the perimeter of each layer corresponds to the other. The layers may then be stitched together using thread along the perimeter of the mask to form seam 31, or alternatively may be adhesively attached together along the perimeter of the mask to form seam 31. In another embodiment, the two or more layers may be attached using adhesive along the surface of each layer and mating two layers together. Two or more layers may also be attached by needle-punching in areas inside the perimeter of the 5layers.

In one embodiment, the layers are attached (such as sewn) together prior to being cut into the desired shape. In another embodiment, the layers are cut to the desired shape prior to being attached (such as sewn) together. In another embodiment, one or more openings 24*a*, 24*b*, 26, and 27 are formed using a cutting tool or blade. Radial slits 32 and 33 may also be made at points along the perimeter of the mask at any point during the process, but preferably this is done prior to forming the seam 31 of the mask. The exposed portions of openings 24*a*, 24*b*, 26, and 27 may also be closed by stitching or adhesive, for example.

The mask is then placed inside container 23 along with instructions 28 and optional spray bottle 22 and dropper bottle 21 to complete the kit 25.

Therapeutic Compositions

The articles of the present invention include one or more optional treatment compositions or therapeutic compositions for application to the skin. Herein, "a treatment composition" or "therapeutic composition" refers to both a first and second treatment composition which may be housed in a spray bottle 22 or dropper bottle 21 or impregnated within the packaged mask 20.

The treatment composition may be provided via a variety of means. The treatment composition may be provided in liquid form and soaked into the multi-layered mask. The mask may then be packaged and sealed for delivery to consumers and immediate use upon opening of the sealed package. Alternatively, the treatment composition may be dried following application for re-wetting by the consumer prior to application. In yet another embodiment of the present invention, the treatment composition and the multi-layered mask may be packaged separately to be combined by the consumer prior to application to the skin. In such instances the treatment composition may be provided either dry or in liquid form. The treatment composition may be provided to the mask by impregnating the treatment composition into the mask, for example, by admixing the treatment composition with the water or other solutions. The treatment composition may also be provided to the mask by depositing the treatment composition upon the surfaces of mask.

The treatment composition of the present invention preferably includes a skin benefit agent to provide a benefit to the skin, in an amount from about 0.01 wt % to about 30 wt %, preferably from about 0.1 wt %~about 20 wt % by weight of the composition. The skin benefit agent of the present invention includes those as known in the art and includes anti-oxidants, cleansing agents, free radical scavengers, moisturizers, chronic whitening agents, anti-acne agents, anti-dandruff agents, anti-aging agents, softeners, anti-wrinkle agents, keratolic agents, anti-inflamatory agents, oily components, skin texture treatment agents, flavanoids, fresheners, healing agents, liporegulators, vascular protectors, anti-bacterial agents, anti-fungal agents, anti-perspirant agents, deodorants, skin conditioners, anesthetics, nourishing agents, sebum absorbers, and moisture absorbers. The ingredients are described in more detail herein.

Anti-oxidants and radical scavengers are especially useful for providing protection against UV radiation which can cause increased scaling or texture changes in the stratum corneum and against other environmental agents which can cause skin damage and may be optionally included in the treatment composition. Anti-oxidants and radical scavengers such as tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, amines (i.e., N,N-diethylhydroxylamine, amino-guanidine), sulfhydryl compounds (i.e., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from flavonoids and tocopherol sorbate and other esters of tocopherol, more preferably tocopherol sorbate. For example, the use of tocopherol sorbate in topical compositions and applicable to the present invention is described in U.S. Pat. No. 4,847,071, Bissett et al, issued Jul. 11, 1989 which is incorporated by reference.

Chronic whitening agents useful herein refer to active ingredients that not only alter the appearance of the skin, but further improve hyperpigmentation as compared to pretreatment. By definition, chronic is referred to continued topical application of the composition over an extended period during the subject's lifetime, preferably for a period of at least about one week, more preferably for a period of at least about one month, even more preferably for at least about three months, even more preferably for at least about one year. Typically, applications would be on the order of about once per day over such extended periods, while application rates can vary from about once per week up to about three times per day or more.

Useful chronic whitening agents useful herein include ascorbic acid compounds, vitamin B3 compounds, azelaic acid, butyl hydroxy anisole, gallic acid and its derivatives, glycyrrhizinic acid, hydroquinoine, kojic acid, arbutin, mulberry extract, ergothioneine, and mixtures thereof. Among them, preferred are ascorbic acid compounds, vitamin B3 compounds, and mixtures thereof. Use of combinations of chronic whitening agents are believed to be advantageous in that they may provide whitening benefit through different mechanisms.

Anti-acne actives can be effective in treating and preventing acne vulgais, a chronic disorder of the pilosebaceous follicles. Preferred anti-acne agents optionally included in the treatment composition include salicylic acid, 4-methoxysalicylic acid, benzoyl peroxide, lactic acid, metronidazole, panthenol, retinoic acid and its derivaties, sulphur, triclosan, and mixtures thereof.

Anti-aging agents or anti-wrinkle agents useful herein include, for example, peptides. As used herein, "peptides" refers to both the naturally occurring peptides and synthesized peptides, including but not limited to, di-, tri-, tetra-, and pentapeptides and derivatives thereof. Also useful herein are naturally occurring and commercially available compositions that contain peptides. Suitable dipeptides for use herein include Carnosine® (beta-ala-his). Suitable tripeptides for use herein include, gly-his-lys, arg-lys-arg, his-gly-gly. Preferred tripeptides and derivatives thereof include palmitoyl-gly-his-lys, which may be purchased as Biopeptide CL® (100 ppm of palmitoyl-gly-his-lys commercially available from Sederma, France); Peptide CK (arg-lys-arg); PEPTIDE CK+ (ac-arg-lys-arg-NH2); and a copper derivative of his-gly-gly sold commercially as IAMIN, from Sigma (St. Louis, Mo.). Tetrapeptides and pentapeptides are also suitable for use herein. A preferred commercially available pentapeptide derivative composition is palmitoyl-lys-thr-thr-lys-ser (commercially available from Sederma France). When included in the present compositions, peptides are preferably included in amounts of from about 1×10-6% to about 10%, more preferably from about 1×10-6% to about 0.1%, even more preferably from about 1×10-5% to about 0.01%, by weight of the composition.

The treatment composition of the present invention may contain an anti-inflammatory agent as a skin benefit agent. Anti-inflammatory agents enhance the skin appearance benefits, by for example, contribution of uniformity and acceptable skin tone and/or color and are optionally included in the treatment composition of the present invention as well. Preferably, the anti-inflammatory agent includes a steroidal anti-inflammatory agent and a non-steroidal anti-inflammatory agent. Preferred steroidal anti-inflammatory for use is hydrocortisone. The variety of compounds encompassed by this group is well-known to those skilled in the art. For detailed disclosure of the chemical structure, synthesis, side effects, etc. of non-steroidal anti-inflammatory agents, reference may be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology, 1, R. A. Scherrer, et al., Academic Press, New York (1974), each incorporated herein by reference. So-called "natural" anti-inflammatory agents are also useful. Such agents may suitably be obtained as an extract by suitable physical and/or chemical isolation from natural sources (i.e., plants, fungi, by-products of microorganisms).

Oily components useful herein can deliver skin conditioning benefits such as smoothness and softness to the skin. Oily components useful herein include, for example, fatty alcohols, silicone oils, mineral oil, petrolatum, C7-40 straight and branched hydrocarbons such as isohexadecane, C1-30 alcohol esters such as isopropyl isostearate, glycerides, alkylene glycol esters, propoxylated and ethoxylated derivatives, sugar ester such as sucrose polycottonseedate, vegetable oils such as coconut oil, hydrogenated vegetable oils, animal fats and oils, and C4-20 alkyl ethers of polypropylene glycols, C1-20 carboxylic acid esters of polypropylene glycols, and di-C8-30 alkyl ethers. Hydrophobic nonionic surfactants, which are those being water-insoluble and having an HLB value of less than 10, can be used as oily components. Hydrophobic nonionic surfactants useful herein include, for example, cetearyl glucoside, steareth-2, laureth-4, sucrose cocate, sorbitan monoisostearate, sorbitan diisostearate, sorbitan sesquiisostearate, sorbitan monooleate, sorbitan dioleate, sorbitan sesquioleate, glyceryl monoisostearate, glyceryl diisostearate, glyceryl sesquiisostearate, glyceryl monooleate, glyceryl dioleate, glyceryl sesquioleate, diglyceryl diisostearate, diglyceryl dioleate, diglycerin monoisostearyl ether, diglycerin diisostearyl ether, and mixtures thereof.

The treatment composition may optionally include a skin texture treatment agent. Skin texture treatment agents help repair and replenish the natural moisture barrier function of the epidermis, thereby providing skin benefits such as texture improvement. Skin texture improvement agents useful herein are niacinamide, nicotinic acid and its esters, nicotinyl alcohol, panthenol, panthenyl ethyl ether, n-acetyl cysteine, n-acetyl-L-serine, phosphodiesterase inhibitors, trimethyl glycine, tocopheryl nicotinate, and vitamin B3 and analogues or derivatives, and mixtures thereof.

Flavonoid compounds useful herein include unsubstituted flavanones, substituted flavanones, unsubstituted flavones, substituted flavones, unsubstituted chalcones, substituted chalcones, unsubstituted isoflavones, and substituted isoflavones. By the term "substituted" as used herein means flavonoid compounds wherein one or more hydrogen atoms of the skeleton structure as described above has been independently replaced with hydroxyl, C1-C8 alkyl, C1-C4 alkoxyl, O-glycoside, and the like or a mixture of these substituents. Flavonoid compounds particularly useful herein are selected from the group consisting of substituted flavanones, substituted flavones, substituted chalcones, substituted isoflavones, and mixtures thereof. In one particularly preferred embodiment of the present invention, the glycoside flavonoid is selected from the group consisting of glucosyl hesperidin, glucosyl rutin, glucosyl myricitrin, glucosyl isoquercitrin, glucosyl quercitrin, methyl hesperidin, and mixtures thereof. These glucoside flavonoid compounds can be obtained by bio-chemical methods from related natural flavonoid compounds.

The treatment composition of the present invention preferably contains a water-soluble humectant as a skin benefit agent. Water-soluble humectants are preferably included to provide moisturizing benefit to the skin. Further, water-soluble humectants may help the dispersion of the water-soluble thickening agents, and dissolving/dispersion of other components which are relatively difficult to process in an aqueous carrier.

Water-soluble humectants useful herein include polyhydric alcohols such as glycerin, diglycerin, propylene glycol, dipropylene glycol, butylene glycol, hexylene glycol, sorbitol, ethoxylated glucose, 1,2-hexane diol, hexanetriol, erythritol, trehalose, xylitol, maltitol, maltose, glucose, fructose, sodium chondroitin sulfate, sodium hyaluronate, sodium adenosin phosphate, sodium lactate, pyrrolidone carbonate, glucosamine, cyclodextrin, and mixtures thereof. Water-soluble humectants useful herein also include water-soluble alkoxylated nonionic polymers such as polyethylene glycols and polypropylene glycols having a molecular weight of up to about 1000 such as those with CTFA names PEG-200, PEG-400, PEG-600, PEG-1000, and mixtures thereof.

The treatment composition of the present invention may include a skin tone changing agent. The skin tone changing agent may be included in the composition at a level by weight of, from about 0.001% to about 50%, preferably from about 0.1% to about 25%, more preferably from about 1% to about 10%.

The skin tone changing agent useful herein is selected from the group consisting of skin tone changing pigments, reflective particulate material, and mixtures thereof. Skin tone changing agents useful herein are those altering the appearance of the color and/or tone of the skin including, but not limited to, skin whitening. The skin tone changing agents have a particle size of, preferably at least about 100 nm. The skin tone changing pigments useful herein include, for example, talc, mica, silica, magnesium silicate, titanium oxide, zinc oxide, and titanium oxide coated mica.

The treatment compositions of the present invention are preferably in liquid form and include a water-soluble thickening polymer. The water-soluble thickening polymers herein are water-soluble or water miscible polymers, have the ability to increase the viscosity of the composition, and are compatible with other components used in the composition. The water-soluble thickening polymer is selected so that the liquid composition of the present composition has the desired viscosity of from about 500 mPa·s to about 60,000 mPa·s, preferably from about 1000 mPa·s to about 30,000 mPa·s, more preferably from about 2000 mPa·s to about 15,000 mPa·s. A viscosity may be measured by a commercially available viscometer like BROOKFIELD DV II+Viscometer with Helipath T-C bar type spindle (BROOKFIELD ENGINEERING LABORATORIES, INC.) at 5 rpm/min at 25° C. Water-soluble thickening polymers useful herein include anionic polymers and nonionic polymers. The water-soluble thickening polymers useful herein include, for example, acrylic polymers, polyalkylene glycol polymers having a molecular weight of more than about 10000, celluloses and derivatives thereof such as hydroxyethyl cellulose, polyvinylpyrrolidone, polyvinyl alcohol, gums such as guar gum and xanthan gum, carragenan, pectin, agar, quince seed (*Cydonia oblonga* Mill), starch (rice, corn, potato, wheat), algae colloids (algae extract), dextran, succinoglucan, pulleran, carboxymethyl starch, methylhydroxypropyl starch, sodium alginate, and alginic acid propylene glycol esters. Neutralizing agents may be included to neutralize the anionic thickening agents described hereinabove. Nonlimiting examples of such neutralizing agents include sodium hydroxide, potassium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof.

The treatment composition of the present invention comprises optionally a hydrophilic surfactant. The hydrophilic surfactant may be included in the composition at a level by weight of from about 0.01% to about 10%, preferably from about 0.05% to about 5%, more preferably from about 0.1% to about 2%.

Hydrophilic surfactants useful herein are those being water-soluble, and preferably have an HLB value of above 10. Hydrophilic surfactants useful herein include, for example, any cosmetically acceptable surfactants, i.e., nonionic surfactants, cationic surfactants, anionic surfactants, zwitterionic surfactants, amphoteric surfactants, and mixtures thereof. Among them, preferred herein are cosmetically acceptable nonionic surfactants in view of reduced skin irritation and conditioning benefits. Hydrophilic nonionic surfactants useful herein include, for example, PEG-100 stearate, polysorbate-20, polysorbate-60, seteareth-21, isoceteth-20, and oleth-20, laureth-23, ceteareth-12, steareth-100, PEG 40 hydrogenated castor oil, PEG-60 hydrogenated castor oil, and mixtures thereof.

The compositions of the present invention may include a cooling agent. Cooling agent useful herein include natural cooling agents such as menthol, peppermint oil, camphor, borneol, eucalyptol, eucalyptus oil, tea tree oil, ketals, carboxamides, cyclohexanol derivatives, cyclohexyl derivatives and mixtures thereof.

The treatment compositions of the present invention when in their preferred liquid form further include an aqueous carrier. The level and species of the carrier are selected according to the compatibility with other components, and other desired characteristic of the product.

The aqueous carrier may be included in the composition at a level by weight of from about 0.1% to about 30%, preferably from about 1% to about 25%, more preferably from about 30% to about 10%.

Carriers useful in the present invention include water and water solutions of lower alkyl alcohols. Lower alkyl alcohols useful herein are monohydric alcohols having 1 to 6 carbons, more preferably ethanol. Preferably, the aqueous carrier is substantially water. Deionized water is preferably used. Water from natural sources including mineral cations can also be used, depending on the desired characteristic of the product.

The pH of the liquid compositions is preferably from about 4 to about 8. When skin benefit agents are included in the liquid composition, the pH may be adjusted to that which provides optimum efficacy of the skin benefit agents. Buffers and other pH adjusting agents can be included to achieve the desirable pH. Suitable pH adjusters herein include acetates, phosphates, citrates, triethanolamines and carbonates.

In addition to the above described components, the composition of the present invention may further include preservatives and preservative enhancers such as water-soluble or dispersible preservatives.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

I claim:

1. A kit for treating skin, comprising
   a) a reusable facial mask having a skin contacting layer and an insulating layer, the skin contacting layer having a skin contacting surface and an inside surface and the insulating layer having an outside surface and an inside surface, the inside surface of the skin contacting layer being in substantial contact with the inside surface of the insulating layer, wherein the two layers are secured together along the perimeter of the layers to form a multiple layered article;
   b) a container which houses the mask;
   c) a treatment composition to apply to the mask; and, d) written or graphic instructions for use of the mask comprising the following steps:
   moistening the layered article with water or the treatment composition,
   heating or cooling the layered article,
   placing the layered article on the skin for an amount of time,
   removing the layered article from the skin, and,
   washing the layered article to use it again,
wherein the facial mask further comprises a fiberglass layer.

2. The kit of claim 1, wherein the instructions are provided in the form of an html address which provides the steps for use of the mask.

3. The kit of claim 1, wherein the instructions are provided in the form of an html address which includes a video demonstration of use of the mask.

4. The kit of claim 1, further comprising one or more photographs or drawings depicting one or more steps of use of the mask.

5. The kit of claim 1, wherein the insulating layer comprises foam or neoprene.

6. The kit of claim 1, wherein the step of heating the layered article comprises microwaving the article.

7. The kit of claim 1, wherein the step of cooling the layered article comprises placing the article in the freezer or the refrigerator.

8. The kit of claim 1, wherein the step of moistening the layered article comprises placing the article in the container along with an amount of water.

9. The kit of claim 8, wherein the step of heating the layered article comprises subjecting the container having the layered article and water within it to microwaves.

10. The kit of claim 8, wherein the step of cooling the layered article comprises placing the container having the layered article and water within it into a refrigerator or freezer.

11. The kit of claim 1, wherein the step of washing the layered article comprises machine washing.

12. The kit of claim 1 wherein the insulating layer has a k value of about 0.01 to about 1 W/m K.

13. The kit of claim 1, wherein the facial mask further comprises a mesh layer with a total open area of between 30% and 95%.

14. The kit of claim 1, wherein the facial mask is a single article having a substantially circular shape with one or more openings to accommodate the eyes, mouth or nose of a user.

15. The kit of claim 14, wherein the facial mask includes one or more slits starting at the perimeter of the mask and ending at a point closer to the center of the mask in order to accommodate a number of face sizes.

16. The kit of claim 15, wherein the instructions further comprise a step of keeping the layered article on the skin for about thirty minutes to about one hour.

17. The kit of claim 1, wherein the insulating layer comprises a neoprene layer.

18. The kit of claim 1, wherein the facial mask further comprises a gel layer.

19. A method of treating the face, comprising:
   providing a reusable, washable facial mask comprising a skin contacting layer and an insulating layer, the skin contacting layer having a skin contacting surface and an inside surface and the insulating layer having an outside surface and an inside surface, the inside surface of the skin contacting layer being in substantial contact with the inside surface of the insulating layer wherein the two layers are secured together along the perimeter of the layers to form a multiple layered article,
   moistening the layered article with water or a treatment composition,
   heating or cooling the layered article,
   placing the layered article on the skin for an amount of time, and,
   removing the layered article from the skin
wherein the facial mask further comprises a fiberglass layer.

* * * * *